United States Patent [19]

Mölling et al.

[11] Patent Number: 5,093,477
[45] Date of Patent: Mar. 3, 1992

[54] RAPIDLY CLEAVABLE SUBSTRATE FOR HIV PROTEASE

[75] Inventors: Karin Mölling, Berlin; Stephan Henke, Hofheim am Taunus; Gerhard Breipohl, Frankfurt am Main; Wolfgang König, Hofheim am Taunus, all of Fed. Rep. of Germany

[73] Assignee: Hoechst Aktiengesellschaft, Frankfurt am Main, Fed. Rep. of Germany

[21] Appl. No.: 449,766

[22] Filed: Dec. 13, 1989

[30] Foreign Application Priority Data

Dec. 15, 1988 [DE] Fed. Rep. of Germany ....... 3842197

[51] Int. Cl.$^5$ .................. C12Q 1/37; C07K 7/06; C07D 207/02
[52] U.S. Cl. .................. 530/328; 530/329; 435/23; 514/15; 514/16; 548/335; 436/86
[58] Field of Search .................. 435/23; 530/328, 329; 514/15, 16; 548/535; 436/86

[56] References Cited

U.S. PATENT DOCUMENTS 4,952,493  8/1990  Kettner et al. .................. 435/23
5,011,910  4/1991  Marshall et al. .................. 530/329

FOREIGN PATENT DOCUMENTS 0271865  12/1987  European Pat. Off. .
0314023  5/1989  European Pat. Off. .

OTHER PUBLICATIONS

D. Heinova et al., *Chemical Abstract* 113:293, Abstract #20146, 1990, Abstract of Czech. CS 261,172, Jun. 15, 1989.
Vasella et al., *Helvetica Chimica Acta*, vol. 66, No. 4, pp. 1241–1252 (1983).
Schneider et al., *Cell*. vol. 54, pp. 363–368 (Jul. 29, 1988).

*Primary Examiner*—Jeffrey E. Russel
*Assistant Examiner*—Stephen Walsh
*Attorney, Agent, or Firm*—Finnegan, Henderson, Farabow, Garrett, and Dunner

[57] ABSTRACT

A rapidly cleavable substrate for HIV protease Hepta- to nona-peptides of the formula $$A-B-C-D-E-Opr-F-G-H,$$

in which A is absent or represents Val, Ile or Thr, B denotes Ser, Thr or Phe, D denotes Asp or Ala, E denotes Tyr or Phe, Opr denotes 5-oxaproline, F denotes Ile, Leu, Val, Thr or Gln, G denotes Val, Ile, Ser or Arg, and H is absent or represents Gln, Glu, Pro or Thr, as well as the salts thereof are used for locating and detecting HIV protease and for testing possible inhibitors of HIV protease. They are prepared by known methods of peptide chemistry, preferably by means of solid-phase synthesis.

5 Claims, No Drawings

RAPIDLY CLEAVABLE SUBSTRATE FOR HIV PROTEASE

DESCRIPTION

A rapidly cleavable substrate for HIV protease

The invention relates to hepta-peptides to nona-peptides and to the use thereof for locating and detecting HIV protease and for testing possible inhibitors of HIV protease.

HIV protease, a retrovirus protease, cleaves gag and gagpol precursor proteins of AIDS viruses into the functional proteins. This correct cleavage is necessary for infection with HIV [N. E. Kohl, E. A. Emini, W. A. Schleif, L. J. Davis, J. C. Heimbach, R. A. F. Dixon, E. M. Scolnick and I. S. Sigal, Proc. Natl. Acad. Sci. USA 85 (1988) 4686–4690]. The protease is encoded in the 5' region of the pol gene (for example HTLV-III pol (69–167)). It is a specific aspartyl protease which can be inhibited by the aspartyl protease inhibitor pepstatin. Good inhibitors of this HIV protease which are able to enter cells have importance for the treatment of HIV-infected patients.

The enzyme is composed of only 99 amino acids and evidently eliminates itself from the pol gene by hydrolysis of the two Phe-Pro linkages in positions 68–69 and 167–168 [M. C. Graves, J. J. Lim, E. P. Heimer and R. A. Kramer, Proc. Natl. Acad. Sci. USA 85 (1988) 2449–2453; J. Hansen, S. Billich, T. Schulze, S. Sukrow and K. Moelling, The EMBO J. 7 (1988) 1785–1791; E. P. Lillehoj, F. H. R. Salazar, R. J. Mervis. M. G. Raum, H. W. Chan, N. Ahmad and S. Venkatesan, J. Virology 62 (1988) 3053–3058; J. Schneider and S. B. H. Kent, Cell 54 (1988) 363–368].

The substrates which have hitherto been used for HIV protease are the following peptides, which were cleaved at the indicated points [J. Schneider and S. B. H. Kent, Cell 54 (1988) 363–368]:

$$\downarrow$$
RRSNQVSQNYPIVQNIQGRR $$\downarrow \qquad \downarrow$$
GHKARVLAEAMSQVTNSATIMMQRGNFRNQRK $$\downarrow$$
DRQGTVSFNFPQVTLWQRPL $$\downarrow$$
RRQIGATLNFPISPIETVRRa

[P. L. Drake, R. F. Nutt, S. F. Brady, V. M. Garsky, T. M. Ciccarone, C.-T. Leu, P. K. Lumma, R. M. Freidinger, D. F. Veber and I. S. Sigal, Biochem. Biophys. Res. Commun. 156 (1988) 297–303]:

$$\downarrow$$

| | |
|---|---|
| HIV-1: | |
| gag-(124–138) | H S S Q V S Q N Y P I V Q N I |
| | V S Q N Y P I V |
| | S Q N Y P I V Q |
| | S Q N Y P I V |
| gag-(357–370) | G H K A R V L A E A M S Q V |
| gag-(370–383) | V T N T A T I M M Q R G N F |
| gag-(440–453) | S Y K G R P G N F L Q S R P |
| pol-(59–72) | D R Q G T V S F N F P Q I T |
| pol-(162–174) | G C T L N F P I S P I E T |
| pol-(721–734) | A G I R K I L F L D G I D K |
| HIV-2: | |
| gag-(129–142) | S E K G G N Y P V Q H V G G |

A similar protease from the avian sarcoma leukosis virus likewise cleaves the Tyr-Pro linkage [M. Kotler, R. A. Katz, W. Danho, J. Leis and A. M. Skalka, Proc. Natl. Acac. Sci. USA 85 (1988) 4185–4189]:

$$\downarrow$$
T F Q A Y P L R E A
T F Q A F P L R E A

It has now been found, surprisingly, that replacement of Pro in the sequences by 5-oxaproline results in substrates which are cleaved considerably more rapidly by HIV protease. Thus, with these substrates, a result is obtained more rapidly, and less of the HIV proteases, which are difficult to obtain and costly, is required.

The invention relates to hepta-peptides to nona-peptides of the general formula I $$A-B-C-D-E-Opr-F-G-H \qquad (I)$$

in which

A can be absent or represents valine, isoleucine or threonine,

B denotes serine, threonine or phenylalanine,

C denotes leucine, glutamine or phenylalanine,

D denotes asparagine or alanine,

E denotes tyrosine or phenylalanine,

Opr denotes the radical of isoxazolidine-3-carboxylic acid (=5-oxaproline),

F denotes isoleucine, leucine, valine, threonine or glutamine,

G denotes valine, isoleucine, serine or arginine and

H can be absent or denotes glutamine, glutamic acid, proline or threonine, as well as the salts thereof.

Preferred peptides of the formula I are those in which

A is absent or represents valine,

B denotes serine,

C denotes glutamine or phenylalanine,

D denotes asparagine,

E denotes tyrosine or phenylalanine,

F denotes isoleucine or glutamine,

G denotes valine or isoleucine and

H is absent or denotes glutamine.

Peptides of the formula I which may be mentioned in particular are those in which A is absent, B denotes serine, C denotes phenylalanine, D denotes asparagine, E denotes phenylalanine, F denotes glutamine, G denotes isoleucine and H is absent.

Suitable salts are, in particular, alkali metal and alkaline earth metal salts, salts with amines and salts with inorganic or organic acids such as, for example, hydrochloric acid, hydrobromic acid, sulfuric acid, maleic acid, acetic acid, trifluoroacetic acid or fumaric acid.

The invention additionally relates to a process for the preparation of peptides of the formula I, which comprises
a) reacting a fragment with a C-terminal free carboxyl group or the activated derivative thereof with a corresponding fragment with an N-terminal free amino group or
b) synthesizing the peptide stepwise, eliminating one or more protective groups temporarily introduced to protect other functionalities where appropriate in the compound obtained as in (a) or (b), and converting the peptides of the formula I obtained in this way into the salt thereof where appropriate.

The peptides of the present invention were prepared by generally known methods of peptide chemistry, see, for example, Houben-Weyl, Methoden der organischen Chemie [Methods of organic chemistry], volume 15/2, preferably by means of solid-phase synthesis such as, for example, described by B. Merrifield, J. Am. Chem. Soc. 85, 2149 (1963), R.C. Sheppard Int. J. Peptide Protein Res. 21, 118 (1983) or in EP-A-231,752 (HOE 86/F 099J) or proposed in European Patent Application No. 88 111011.8 (HOE 87/F 204) or by equivalent known methods. Used as α-amino-protective group are urethane protective groups such as, for example, the tert.-butyloxycarbonyl (Boc) or fluorenylmethyloxycarbonyl (Fmoc) protective group. If necessary to prevent side reactions or for the synthesis of specific peptides, the functional groups in the side chain of amino acids are additionally protected by suitable protective groups (see, for example, T. W. Greene, "Protective Groups in Organic Synthesis" or EP-A-231,752).

The peptides according to the invention are used for locating and detecting HIV protease and for testing possible inhibitors of HIV protease. They are distinguished by being very rapidly cleaved by HIV protease, as shown by the cleavage experiments hereinafter, for which various batches of a cloned HIV protease solution were used.

A) General procedure for testing inhibitors of HIV protease with Ser-Phe-Asn-Phe-Opr-Gln-Ile a) Preparation of the substrate solution:
2 mg of Ser-Phe-Asn-Phe-Opr-Gln-Ile are dissolved in 1 ml of MGTE15 buffer (possibly using ultrasound) and subsequently filtered through a sterile filter (0.45 μm).

b) Preparation of the inhibitor solution:
2.5 times the desired molarity of the inhibitor per ml of solution are weighed in and dissolved in DMSO (10% of the final volume). The solution is diluted to the final volume with MGTE15 buffer and filtered through a sterile filter (0.45 μm).

c) Preparation of the protease solution:
5 μl of the HIV protease solution are diluted with MGTE25 buffer as required.

d) Test procedure:
10 μl portions of the substrate solution are pipetted into test tubes (16×100) with screw caps. 10 μl of MGTE15 buffer which contains 10% DMSO are pipetted into the blank. 10 μl portions of the inhibitor solutions are added to the remaining test tubes. These samples are incubated at 37° C. for 5–10 minutes and then 5 μl of the protease solution are added to each. After reaction at 37° C. for 2 hours, 10 or 20 μl of each sample (depending on the sensitivity of the HPLC apparatus) are removed by pipette, placed in microvials and diluted with 120 μl of the HPLC solvent.

e) Conditions for HPLC analysis:
Solvent system: 80% 0.1 M phosphoric acid pH 2.5. 20% (w/w) acetonitrile
Column: Merck ®LICHROSORB RP18 (5 μm) 250×4
Flow rate: 1 ml/min
Column temperature: 42° C.
Detector parameters: 215 nm, 0.08 AUF, 18.2° C.
Analysis time: 11 minutes
Retention time of the substrate: 8.1 minutes
Retention time of the N-terminal tetrapeptide: 3.9 minutes f) Solvents required:
1) MGTE15 buffer:
  20 mM morpholinoethanesulfonic acid (MES)
  15% (w/v) glycerol
  0.01% (v/v) Triton×100
  5 mM EDTA
  0.5 M NaCl
  1 mM phenylmethanesulfonyl fluoride (PMSF)
2) MGTE25 buffer:
  Composition similar to that of MGTE15 buffer with
  the following difference:
  25% (w/v) glycerol,
  plus 1 mM dithiothreitol (DTT)

MES, EDTA, NaCl, DTT and PMSF are weighed into an Erlenmeyer flask, dissolved in a little water and adjusted to pH 6. The appropriate amount of glycerol is weighed into a graduated flask and Triton×100 is pipetted in. The aqueous solution is transferred into the graduated flask, which is made up to the mark with water.

3) HPLC solvent:
A 0.1 M solution of orthophosphoric acid (FLUKA extra pure grade) is prepared. This solution is adjusted to exactly pH 2.5 with triethylamine (FLUKA extra pure grade). The weight of the solution is determined, and the appropriate amount of acetonitrile (N.B.) is weighed in. Thoroughly mix and degas with helium 5.0 for about 5 minutes.

g) Evaluation:
Under the conditions chosen here, the heptapeptides are separated from the N-terminal tetrapeptide produced in the enzymatic cleavage. The % content of the tetrapeptide peak relative to the tetrapeptide+heptapeptide total corresponds to the proportion cleaved.

B) Procedure for HIV protease kinetics (Tab. 1–4)

10 μl of substrate solution (2–4 mg/ml) in MGTE15 buffer and 10 μl of MGTE15 buffer which contains 10% dimethyl sulfoxide are combined and incubated at 37° C. for 5–10 minutes. 5 μl of the HIV protease solution in MGTE25 buffer are added to this, and the mixture is shaken at 37° C. 2 μl portions are removed after 5, 10, 20, 40, 80, 160 and 360 minutes and pipetted into 50 μl of HPLC solvent (stops the reaction). The microliter syringe is used to load the total amount onto the HPLC column. HPLC conditions as in A).

C) Procedure for the HIV protease kinetics (Tab. 6) 10 μl of substrate solution (2 mg/ml) in MGTE15 buffer and 10 μl of MGTE15 buffer are combined and incubated at 37° C. for 5-10 minutes. 5 μl of HIV protease No. II (diluted 1:4 with MGTE25 buffer) are added to this, and the mixture is shaken at 37° C. Subsequent procedure as in B).

HPLC conditions:
Column: Merck HIBAR ®LICHROSORB RP8 (7 μm) 250×4
Flow rate: 1 ml/min for SFNFPQI and SFNFOQI 0.5 ml/min for VSQNYPIVQ and VSQNYOIVQ. Otherwise as in Ae).

| Retention times for | SFNFPQI: | 6.7 min |
|---|---|---|
| | SFNFOQI: | 6.5 min |
| | SFNF: | 3.7 min |
| | VSQNYPIVQ: | 5.3 min |
| | VSQNYOIVQ: | 5.5 min |
| | VSQNY: | 4.6 min. |

Tables 1 and 2 show the cleavage of Ser-Phe-Asn-Phe-Pro-Gln-Ile (SFNFPQI) and Ser-Phe-Asn-Phe-Opr-Gln-Ile (SFNFOQI) under the same conditions. The cleavage of the peptides into the N-terminal tetrapeptide and the C-terminal tripeptide is followed by HPLC. Whereas there was about 4% cleavage of the Pro-containing hepta-peptide after 5 minutes' cleavage time (Tab. 1), the Opr-containing heptapeptide had already been 40–43% cleaved in the same time (Tab. 2). Thus, the cleavage takes place about 10 times as fast with the substrates according to the invention. Tables 3 and 4 show that even highly diluted HIV protease solutions give good cleavage rates with the new substrates. That it is also possible to inhibit the cleavage of these Opr-containing sequences is evident from Table 5, which shows that pepstatin A inhibits HIV protease with an $IC_{50}$ of about $10^{-6}$ M. Table 6 shows a direct comparison of the heptapeptides described above with the nonapeptides Val-Ser-Gln-Asn-Tyr-Pro-Ile-Val-Gln (VSQNYPIVQ) and Val-Ser-Gln-Asn-Tyr-Opr-Ile-Val-Gln (VSQNYOIVQ).

TABLE 1

Cleavage of Ser—Phe—Asn—Phe—Pro—Gln—Ile (4 mg/ml) with HIV protease No. II (5 μl)

| | % cleavage | |
|---|---|---|
| Time (min) | Experiment A | Experiment B |
| 5 | 4.00 | 4.15 |
| 10 | 8.19 | 7.54 |
| 20 | 14.57 | 14.35 |
| 40 | 23.40 | 23.00 |
| 80 | 39.43 | 37.68 |
| 160 | 58.39 | 57.11 |

TABLE 1-continued

Cleavage of Ser—Phe—Asn—Phe—Pro—Gln—Ile (4 mg/ml) with HIV protease No. II (5 μl)

| | % cleavage | |
|---|---|---|
| Time (min) | Experiment A | Experiment B |
| 320 | 70.16 | 72.51 |

TABLE 2

Cleavage of Ser—Phe—Asn—Phe—Opr—Gln—Ile (4 mg/ml) with HIV protease No. II (5 μl)

| | % cleavage | |
|---|---|---|
| Time (min) | Experiment A | Experiment B |
| 5 | 40.43 | 43.32 |
| 10 | 62.10 | 65.06 |
| 20 | 81.56 | 84.39 |
| 40 | 95.98 | 95.79 |
| 80 | 98.82 | 98.76 |
| 160 | 100.00 | 100.00 |
| 320 | 99.48 | 99.55 |

TABLE 3

Cleavage of Ser—Phe—Asn—Phe—Opr—Gln—Ile (2 mg/ml) with diluted HIV protease No. II (5 μl)

| | % cleavage | | | |
|---|---|---|---|---|
| Time (min) | 1:10 | 1:20 | 1:30 | 1:40 |
| 5 | 9.71 | 4.92 | 3.42 | 2.57 |
| 10 | 17.29 | 9.16 | 6.12 | 4.50 |
| 20 | 29.13 | 15.96 | 10.50 | 7.63 |
| 40 | 48.34 | 27.23 | 17.82 | 12.57 |
| 80 | 70.56 | 44.82 | 30.94 | 21.82 |
| 160 | 88.07 | 64.12 | 48.87 | 35.59 |
| 320 | 90.74 | 70.52 | 57.99 | 43.78 |

TABLE 4

Reaction of Ser—Phe—Asn—Phe—Opr—Gln—Ile (2 mg/ml) after 120 minutes as a function of different concentrations of HIV protease No. II

| | 1:10 (0.1) | 1:20 (0.05) | 1:30 (0.033) | 1:40 (0.025) |
|---|---|---|---|---|
| Reaction [%] | 82.5 | 57.0 | 42.0 | 30.0 |

TABLE 5

HIV protease test with Ser—Phe—Asn—Phe—Opr—Gln—Ile (2 mg/ml) and HIV protease No. I (1:10)

| | Conc. (M) | Cleavage (%) | $IC_{50}$ |
|---|---|---|---|
| Blank | | 33.62 | |
| Pepstatin A | $10^{-4}$ | 1.25 | |
| Pepstatin A | $10^{-5}$ | 4.73 | |
| Pepstatin A | $10^{-6}$ | 18.22 | about $10^{-6}$ M |
| Pepstatin A | $10^{-7}$ | 25.09 | |

TABLE 6

Comparison of the cleavage rate of several substrates (2 mg/ml) with HIV protease No. II (1:4)

| | (% tetrapeptide = % cleavage) | | | |
|---|---|---|---|---|
| Time (min) | SFNFPQI | SFNFOQI | VSQNYPIVQ | VSQNYOIVQ |
| 5 | 0.25 | 30.09 | 3.66 | 10.27 |
| 10 | 4.68 | 47.35 | 6.53 | 20.72 |
| 20 | 7.01 | 69.58 | 11.31 | 40.47 |
| 40 | 11.34 | 89.92 | 20.32 | 60.50 |
| 80 | 19.50 | 100.00 | 31.49 | 88.98 |
| 160 | 34.19 | 100.00 | 55.00 | 100.00 |
| 320 | 48.18 | 100.00 | 62.48 | 100.00 |

EXAMPLE 1

Synthesis of Ser-Phe-Asn-Phe-Opr-Gln-Ile

The target peptide was synthesized stepwise by using a model 430 A peptide synthesizer from Applied Biosystems and using the Fmoc method on a p-benzyloxybenzyl alcohol-resin from Novabicohem which was esterified with Fmoc-Ile-OH (loading about 0.5 mmol/g of resin). 1 g of the resin was employed, and the synthesis was carried out with the aid of a synthesis program modified for the Fmoc method.

The following amino acid derivatives are used: Fmoc-Gln-OH, Fmoc-Opr-OH, Fmoc-Phe-OObt, Fmoc-Asn-OH and Fmoc-Ser(tBu)-OObt. To synthesize Fmoc-Opr-OH, H-Opr-OtBu was synthesized by the method of Vasella et al. (J.C.S. Chem. Comm. 1981, 97–98) and reacted with Fmoc-OSu in dioxane/water (1:1) in the presence of $NaHCO_3$. The subsequent cleavage of the tert.-butyl ester with trifluoroacetic acid provides Fmoc-Opr-OH.

In each case, 1 mmol of the amino acid derivatives with a free carboxyl group was weighed together with 0.95 mmol of HOObt into the cartridges of the synthesizer. These amino acids were preactivated directly in the cartriges by dissolving in 4 ml of DMF and adding 2 ml of a 0.55 molar solution of diisopropylcarbodiimide in DMF. The HOObt esters of the other amino acids were dissolved in 6 ml of NMP and then coupled, just like the amino acids preactivated in situ, to the resin which had previously been deblocked with 20% piperidine in DMF. After the synthesis was complete, the peptide was cleaved off the resin, with simultaneous removal of side-chain protective groups, with trifluoroacetic acid using thioanisole and ethanedithiol as cation traps. The residue obtained after the trifluoroacetic acid had been stripped off was subjected to multiple digestion with ethyl acetate and centrifugation. The remaining residue was chromatographed on an alkylated dextran gel with 10% strength acetic acid. The fractions containing the pure peptide were combined and freeze-dried.

Mass spectrum (FAB): 854 $(M+H^+)$

Amino acid analysis:

Asp: 0.98; Ser: 0.80; Glu: 1.00; Ile: 1.05; Phe: 2.10; NH3 1.76.

EXAMPLE 2 Synthesis of H-Ser-Phe-Asn-Phe-Pro-Gln-Ile-OH

The synthesis was carried out with a model SP 640 semiautomatic peptide synthesizer from Labortec using $N_\alpha$-Fmoc-protected amino acids. 5 g of Fmoc-Ile-benzyloxybenzyl alcohol-resin (loading 0.43 mmol/g) were employed. This entailed the following synthesis steps being carried out in cycles:

1. Elimination of the Fmoc protective group with 20% piperidine/DMF (2×50 ml),
2. washing of the resin with DMF (7×60 ml),
3. coupling on of the Fmoc-amino acid preactivated in situ as HOBt ester (preactivation with diisopropyl carbodiimide in DMF) (5 equivalents of amino acid, HOBt and carbodiimide; 0.15 equivalents of HOObt as indicator for the progress of the reaction),
4. washing with DMF (5×60 ml).

10% of the resin was removed after Fmoc-Pro-OH (5) had been coupled on, and a further 20% of the resin was removed after Fmoc-Phe-OH (2) had been coupled on, for separate eliminations. After the synthesis of the heptapeptide was complete and after elimination of Fmoc and washing of the resin with DMF, DCM and MTB ether, 4.2 g of H-Ser(tBu)-Phe-Asn-Phe-Pro-Gln-Ile-resin were obtained.

The peptide was cleaved off the resin by treatment with 95% trifluoroacetic acid/$H_2O$ (2.5 h at room temperature). The resin was filtered off and washed with 95% TFA. The filtrate was evaporated to dryness, stirred with ether and dried under high vacuum. Yield of crude peptide 1.13 g. Purification was carried out on an alkylated dextran gel with 10% aqueous acetic acid as eluent. The fractions containing the pure peptide were combined and freeze-dried.

Yield: 323 mg

MS(FAB): 852 $(M+H^+)$

Amino acid analysis: Asp: 1.01; Ser: 0.75; Glu: 0.97; Pro: 1.03; Ile: 1.00; Phe: 2.00.

EXAMPLE 3 Synthesis of H-Val-Ser-Gln-Asn-Tyr-Pro-Ile-Val-Gln-OH

The synthesis was carried out in a model 430A automatic peptide synthesizer from Applied Biosystems using isolated Fmoc-amino acid OObt esters or HOBt esters activated in situ. This entailed the following cycles being performed:

1. Elimination of Fmoc with 20% piperidine in DMF
2. Washing of the resin with NMP
3. Coupling on of the Fmoc-amino acid in NMP (Fmoc-Val-OObt, Fmoc-Ile-OObt, Fmoc-Pro-OObt, Fmoc-Tyr(tBu)-OObt, Fmoc-Ser(tBu)-OObt) or in DMF (Fmoc-Asn-OH, Fmoc-Gln-OH amino acids preactivated as HOBt esters in situ with diisopropylcarbodiimide)
4. Washing with NMP The synthesis was carried out on an amide anchoring resin which is described in German Patent Application P 37 43 620.1 (HOE 87/F 386) and to which the Fmoc-Glu-OtBu was coupled via the γ-carboxyl group. This resin provides the C-terminal glutamine on elimination with acid. 500 mg of the Fmoc-Glu(NH-anchor)-OtBu resin were employed.

817 mg of peptide-resin were obtained after the synthesis was complete and elimination of Fmoc. The peptide was cleaved off the resin by treatment with 95% trifluoroacetic acid/$H_2O$ (3 h at room temperature). The resin was filtered off and washed with 95% TFA. The filtrate was evaporated to dryness, stirred with ether and dried under high vacuum. Yield of crude peptide 236 mg. Purification was carried out on alkylated dextran gel with 10% aqueous acetic acid as eluent. The fractions containing the pure peptide were combined and freeze-dried.

Yield: 142 mg

MS(FAB): 1047 $(M+B^+)$

Amino acid analysis: Asp: 1.00; Ser: 0.87; Glu: 2.04; Pro: 1.00; Val: 1.96; Ile: 0.86; Tyr: 0.91.

EXAMPLE 4 Synthesis of H-Val-Ser-Gln-Asn-Tyr-Opr-Ile-Val-Gln-OH

The synthesis was carried out in a model 430A automatic peptide synthesizer from Applied Biosystems using isolated Fmoc-amino acid OObt esters or HOBt esters activated in situ. This entailed the following cycles being performed:

1. Elimination of Fmoc with 20% piperidine in DMF
2. Washing of the resin with NMP 3. Coupling on of the Fmoc-amino acid in NMP (Fmoc-Val-OObt, Fmoc-Ile-OObt, Fmoc-Tyr(tBu)-OObt, Fmoc-Ser(tBu)-OObt) or in DMF (Fmoc-Opr-OH, Fmoc-ASn-OH, Fmoc-Gln-OH amino acids preactivated as HOBt esters in situ with diisopropylcarbodiimide)

4. Washing with NMP

The synthesis was carried out on an amide anchoring resin which is described in German Patent Application P 37 43 620.1 (HOE 87/F 386) and to which the Fmoc-Glu-OtBu was coupled via the γ-carboxyl group. This resin provides the C-terminal glutamine on elimination with acid. 500 mg of the Fmoc-Glu(NH-anchor)-OtBu resin were employed. 820 mg of peptide-resin were obtained after the synthesis was complete and elimination of Fmoc. The peptide was cleaved off the resin by treatment with 95% trifluoroacetic acid/H₂O (3 h at room temperature). The resin was filtered off and washed with 95% TFA. The filtrate was evaporated to dryness, stirred with ether and dried under high vacuum. Yield of crude peptide 260 mg. Purification was carried out on alkylated dextran gel with 10% aqueous acetic acid as eluent. The fractions containing the pure peptide were combined and freeze-dried.

Yield: 69 mg

MS(FAB): 1047 (M+H$^+$)

Amino acid analysis: Opr: 1.01; Asp: 1.00; Ser: 0.88; Glu: 2.07; Val: 1.88; Ile: 0.85; Tyr: 0.44.

We claim:

1. Hepta-peptide to nona-peptide of the formula I $$A-B-C-D-E-Opr-F-G-H \qquad (I)$$

in which

A can be absent or represents valine, isoleucine or threonine,

B denotes serine, threonine or phenylalanine,

C denotes leucine, glutamine or phenylalanine,

D denotes asparagine or alanine,

E denotes tyrosine or phenylalanine,

Opr denotes the radical of isoxazolidine-3-carboxylic acid (=5-oxaproline),

F denotes isoleucine, leucine, valine, threonine or glutamine,

G denotes valine, isoleucine, serine or arginine and

H can be absent or denotes glutamine, glutamic acid, proline or threonine, as well as the salts thereof.

2. A peptide of the formula I as claimed in claim 1, in which

A is absent or represents valine,

B denotes serine,

C denotes glutamine or phenylalanine,

D denotes asparagine,

E denotes tyrosine or phenylalanine,

F denotes isoleucine or glutamine,

G denotes valine or isoleucine and

H is absent or denotes glutamine, as well as the salts thereof.

3. A peptide of the formula I as claimed in claim 1, in which

A is absent,

B denotes serine,

C denotes phenylalanine,

D denotes asparagine,

E denotes phenylalanine,

F denotes glutamine,

G denotes isoleucine and

H is absent, as well as the salts thereof.

4. A method for locating and detecting HIV protease which comprises the use of a peptide of the formula I as claimed in claim 1, or the salt thereof.

5. A method for testing possible inhibitors of HIV protease which comprises use of a peptide of the formula I as claimed in claim 1, or the salt thereof.

* * * * *